United States Patent
Biard et al.

(10) Patent No.: US 6,214,999 B1
(45) Date of Patent: Apr. 10, 2001

(54) METHOD FOR PREPARING BROMOMENTHYL-BIPHENYL DERIVATIVES

(75) Inventors: Michel Biard, Sisteron; Bertrand Castro, Kremlin-Bicêtre, both of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/554,566

(22) PCT Filed: Nov. 9, 1998

(86) PCT No.: PCT/FR98/02383

§ 371 Date: Jul. 14, 2000

§ 102(e) Date: Jul. 14, 2000

(87) PCT Pub. No.: WO99/25681

PCT Pub. Date: May 27, 1999

(30) Foreign Application Priority Data

Nov. 17, 1997 (FR) .................................................. 97 14376

(51) Int. Cl.[7] ...................... C07D 257/04; C07C 255/00; C07C 69/76; C07C 233/00
(52) U.S. Cl. ........................ 548/250; 558/425; 560/102; 564/184
(58) Field of Search ........................ 548/250; 558/425; 560/102; 564/184

(56) References Cited

U.S. PATENT DOCUMENTS 5,621,134 * 4/1997 Katsura et al. ...................... 558/388
6,111,114 * 8/2000 Salibeni et al. ....................... 558/250

FOREIGN PATENT DOCUMENTS 0709369  5/1996  (EP) .

OTHER PUBLICATIONS

Database WPI, Section Ch, Week 9619, Derwent Publications Ltd., London, GB (1996).
Patent Abstracts of Japan, vol. 95, No. 1, Feb. 28, 1995.

* cited by examiner

Primary Examiner—Joseph K. McKane
Assistant Examiner—Joseph Murray
(74) Attorney, Agent, or Firm—Michael D. Alexander

(57) ABSTRACT

The present invention relates to a process for the preparation of 4'-bromomethyl-biphenyl derivatives of the formula:

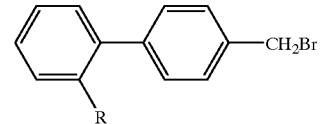

by reacting a 4'-methyl-biphenyl derivative of the formula:

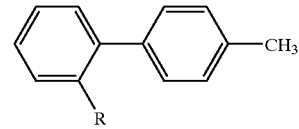

with a brominating agent a in a hydrobromic acid/alkali metal bromate system in a two-phase medium, and under photo-iradiation, where R is as defined in the specification.

23 Claims, 1 Drawing Sheet

METHOD FOR PREPARING BROMOMENTHYL-BIPHENYL DERIVATIVES

The present invention relates generally to the preparation of bromomethylbiphenyl derivatives.

More specifically, the invention relates to a process for preparing 4'-bromomethyl-biphenyl derivatives of general formula:

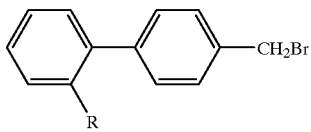

in which R represents:
 a cyano group
 a group:

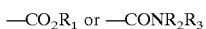

in which $R_1$, $R_2$ and $R_3$, which may be identical or different, represent hydrogen or a linear or branched $C_1$–$C_6$ alkyl group which can be optionally substituted with a halogen atom, a hydroxyl, amino, $C_1$–$C_4$ alkoxy group or with 1 to 3 phenyl groups optionally substituted with 1 to 3 groups chosen from halogen atoms and hydroxyl, nitro, $C_1$–$C_4$ alkyl and $C_1$–$C_4$ alkoxy groups,
a tetrazolyl group of general formula:

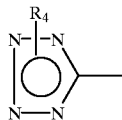

in which $R_4$, in position 1 or preferably in position 2 of the tetrazolyl group, represents hydrogen or a protecting group, in particular a linear or branched $C_1$–$C_6$ alkyl group optionally substituted with 1 to 3 phenyl groups which are themselves optionally substituted with 1 to 3 groups chosen from halogen atoms and hydroxyl, nitro, $C_1$–$C_4$ alkyl and $C_1$–$C_4$ alkoxy groups.

In particular, R can represent a cyano, tetrazolyl or triphenylmethyltetrazolyl group or a group —$CO_2R_1$ in which $R_1$ represents hydrogen or a methyl, ethyl or propyl group.

Among the compounds of formula I which can be prepared by the process of the invention, mention may be made of:
 4'-bromomethyl-2-cyanobiphenyl
 4'-bromomethyl-2-tetrazolylbiphenyl
 4'-bromomethyl-2-carboxybiphenyl
 4'-bromomethyl-2-methoxycarbonylbiphenyl
 4'-bromomethyl-2-N-triphenylmethyltetrazolylbiphenyl However, according to one preferred aspect, the invention relates to the preparation of the compound of formula I in which R represents a cyano group, i.e. 4'-bromomethyl-2-cyanobiphenyl.

The 4'-bromomethylbiphenyl derivatives of formula I are known compounds which have been described in particular in patent applications EP 324 377 and 553 879 or which can be prepared by the processes described therein.

These compounds of formula I constitute intermediates that are particularly useful in the synthesis of many active principles of medicinal products acting in particular against hypertension by a mechanism of inhibition of angiotensin II.

Various methods have recently been proposed for the synthesis of 4'-bromomethyl-2-cyanobiphenyl, these methods being based on a chemically-initiated radical reaction.

For example, mention may be made of patent applications JP 63-23868, 61-92170 and 62-98683 as well as patent applications EP 553 879, 595 150 and 709 369, which all describe, to varying degrees, the bromination of o-tolylbenzonitrile (referred to hereinbelow as OTBN) by means of brominating agents such as N-bromosuccinimide (referred to hereinbelow as NBS), dibromodimethylhydantoin (referred to hereinbelow as DBDMH), N-bromophthalimide or bromine, in the presence of a chemical initiator, generally benzoyl peroxide, t-butyl peroxide, t-butyl perbenzoate or an azobis derivative such as 2,2'-azobis(isobutyronitrile) (referred to hereinbelow as AIBN) or 2,2'-azobis(2,4-dimethylvaleronitrile), the solvent being a $C_5$–$C_7$ alkane, a halogenated $C_1$–$C_4$ aliphatic hydrocarbon such as dichloromethane or carbon tetrachloride, a $C_1$–$C_4$ alkyl ester of acetic acid such as ethyl acetate, or a halogenated aromatic hydrocarbon such as chlorobenzene.

However, these methods comprise both drawbacks and disadvantages, which are occasionally sufficient to exclude them from any industrial-scale use.

For example, the use of peroxide derivatives is found to be very difficult or even dangerous given the explosive nature of this type of product.

Moreover, these processes make use of relatively expensive compounds such as chemical initiators derived from the family of azobis derivatives, or alternatively of products that are sources of pollution since they give rise to unexpected reaction by-products or by-products that are difficult to recycle.

Consequently, the preparation of 4'-bromomethyl-2-cyanobiphenyl via a radical reaction which is not likely to entail pollution, from a minimum amount of compounds, which furthermore is inexpensive and non-hazardous, and according to a method whose industrial implementation is free of major difficulties, remains of unquestionable interest.

To this end, photochemical initiation of a radical-mediated reaction to replace a chemical initiation can, on account of the advantages afforded thereby, represent an approach that is particularly advantageous for offering a solution to the problems previously posed.

Specifically, it is known that chemical initiation:
 a) can be inhibited by the presence of impurities in the starting materials, as can a chemical reaction
 b) is dependent on the temperature; for example, chemical initiators such as benzoyl peroxide or AIBN require a certain working temperature, preferably a temperature greater than 60° C., in particular for the bromination of OTBN
 c) generates decomposition products and, consequently, entails risks of environmental pollution.

A radical-mediated reaction for the preparation of 4'-bromomethyl-2-cyanobiphenyl which involves a photochemical initiation has been suggested in patent applications JP 62-98683 and EP 709 369.

Thus, patent application JP 62-98683 mentions the possibility of photochemical reaction of OTBN with a brominating agent at a temperature of from 0 to 80° C., preferably from 10 to 40° C. and in a fatty acid ester as solvent, ethyl acetate being mentioned more particularly.

In addition, NBS and DBDMH are noted therein as preferred brominating agents and are given therein as examples. Although bromine is also mentioned therein as a brominating agent, no example illustrates its use.

Orientation tests carried out in the context of the development of the present invention have revealed certain drawbacks inherent to this method on account of the nature of the solvent used. Specifically, it has been noted that interfering reactions take place, involving the solvent, i.e. ethyl acetate, giving rise to an increased consumption of the brominating agent, in particular bromine.

Similarly, patent application EP 709 369 reports a process for brominating OTBN, according to which this compound is reacted with bromine at a temperature of from 0 to 100° C., preferably 20 to 80° C. and in the presence of a chemical initiator, i.e. an azobis derivative or benzoyl peroxide and in a halogenated hydrocarbon or a $C_5$–$C_7$ alkane as solvent.

It is also reported therein that the formation of radicals can be ensured by a simple photo-irradiation without the use of a radical initiator.

However, no details whatsoever are given in particular as regards the operating conditions for carrying out this process, which is not exemplified in any way.

In the context of the present invention, an attempt has been made to carry out this radical-mediated photochemical reaction.

It has thus been observed that the bromination of OTBN by bromine with photo-irradiation is slow at temperatures below 50° C. in the conventional organic solvents used for this type of reaction. For example, at 40° C. in dichloromethane, the reaction requires at least 3 hours while at 0° C., the reaction time is greater than 6 hours.

Given that the selectivity of this radical-mediated bromination into monobromo derivative at the expense of the corresponding dibromo derivative increases as the temperature decreases, it appears to be of paramount importance to be able to work at temperatures of less than or equal to 45° C.

Mention will also be made of patent EP 336 567, relating to a process for the photochemical bromination of an alkylarene by means of hydrobromic acid/hydrogen peroxide in a two-phase medium formed from an aqueous phase and an organic phase and at a temperature of from 20 to 80° C., preferably from 60 to 70° C.

The process of this patent can be applied in particular to the bromination of the carbon α to an alkyl group attached to a benzene ring which itself bears a deactivating group such as a cyano group. However, the bromination of OTBN is neither described nor even envisaged in that patent.

After preliminary tests carried out in the course of the development of the present invention, it has been shown that the process of that patent, applied to the bromination of OTBN, requires a very long contact time to obtain high conversion yields.

However, it has now been found, unexpectedly, that it is possible to obtain the compounds of formula I, in particular 4'-bromomethyl-2-cyanobiphenyl, according to a virtually instantaneous radical-mediated photochemical bromination reaction while at the same time avoiding the drawbacks and disadvantages of the previous methods.

According to the invention, the biphenyl derivatives of formula I are obtained by reacting, in a two-phase medium and under the effect of a photo-irradiation, a brominating agent chosen from bromine, N-bromoacetamide, N-bromophthalimide, N-bromomaleimide, an N-bromosulphonamide, N-bromosuccinimide, 1,3-dibromo-5,5-dimethylhydantoin and a hydrobromic acid/alkali metal bromate system with a biphenyl derivative of general formula:

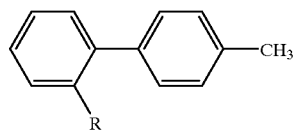

in which R has the same meaning as above, in particular cyano, which gives the desired compound.

The two-phase medium used in the above process consists of water and of one or more water-immiscible organic solvents chosen from solvents generally used in radical-mediated reactions and which offer few possibilities of interaction with the brominating agent.

Such solvents can be, for example, halogenated $C_1$–$C_4$ aliphatic hydrocarbons such as dichloromethane, dichloroethane, chloroform, carbon tetrachloride or tetrachloroethane, or halogenated $C_6$–$C_{10}$ aromatic hydrocarbons such as chlorobenzene or dichlorobenzene.

However, dichloromethane constitutes a preferred organic solvent.

The two-phase medium in question usually comprises from 0.1 to 1 volume of water per volume of organic solvent and is used in a proportion of from 3 to 30 equivalents by volume per equivalent by weight of compound of formula II, in particular of OTBN.

As regards the brominating agent, it is involved in the reaction in a proportion of from 0.5 to 1.4 molar equivalents per molar equivalent of compound of formula II, preferably from 0.9 to 1.2 molar equivalents and better still from 0.95 to 1.1 molar equivalents.

Beyond 1.2 molar equivalents of brominating agent, the tendency to form the corresponding dibromo derivative increases substantially.

This brominating agent is bromine or an organic compound containing bromine, chosen from N-bromoacetamide, N-bromophthalimide, N-bromomaleimide, an N-bromosulphonamide, N-bromosuccinimide (NBS) and 1,3-dibromo-5,5-dimethylhydantoin (DBDMH).

However, NBS, DBDMH and bromine are selected more particularly as preferred brominating agents.

Alternatively, the brominating agent can consist of a hydrobromic acid/alkali metal bromate, preferably sodium bromate, system.

In this case, the alkali metal bromate is used in a proportion of from 0.3 to 0.4 molar equivalent per molar equivalent of compound of formula II.

The reaction according to the invention is usually carried out at a temperature of between 0° C. and 45° C. However, a temperature of between 0° C. and room temperature (about 20 to 25° C.) is preferred, in particular a temperature of between 0° C. and 15° C.

Beyond 50 to 60° C., a relatively large decrease in the selectivity towards the compound of formula I to the benefit of the corresponding dibromo compound is in fact observed.

In order to bring about the formation of radical bromine required for initiation of the reaction of the invention, the photo-irradiation of the reaction mixture is provided by a suitable light source which emits radiation with a wavelength of less than 600 nm. A significant proportion of effective radiation can be obtained from lamps whose main emission is in the range from 350 to 600 nm.

Thus, it is possible, for example, to use a medium-pressure mercury vapour lamp emitting mainly in this wavelength range.

The model of reactor used to carry out the process of the invention also contributes significantly towards the efficacy of the irradiation along with certain other factors such as the ratio of the reaction volume to the surface area illuminated or the distance from the light source to the reaction medium.

The choice of the geometry of this reactor is moreover associated with the possibility of arranging the lamp in the most appropriate manner to optimize the irradiation.

Depending on the case, it is possible, for example, to design the reactor in the form of a simple bent U tube or a helical tube such that the lighting system can be positioned in the immediate vicinity of this reactor.

Preferentially, the reactor chosen is of a type which offers the possibility of arranging the lamp coaxially, for example a reactor in the form of a coil or of a circular tube structure.

In order to reduce even further the light radiation losses, reflectors can also be added.

What is more, it is imperative to take into account factors capable of impairing the efficacy of the luminous flux per unit of surface area to be irradiated, and this is done by using reactors whose model is adapted in the most appropriate manner.

Consequently, the device intended for carrying out the process of the invention will be chosen or modified so as to minimize or eliminate the volumes of reaction mixture which do not directly receive light radiation. For this reason, the choice of reactor will preferably be made from reactors of circular type or in the form of a coil so as to be able to place the lamp coaxially.

A system capable of producing stirring or efficient turbulence of the reaction mixture will also be provided so as to increase the possibilities of passing this mixture through an illuminated zone of the reactor.

The process of the invention thus described takes place over a period of about 1 to 2 hours according to the reaction temperature applied and the duration of the reagent-introduction phase, in most cases over a period of about 1.5 hours.

Thus, at temperatures of about 35° C. to 45° C., the reaction is complete in 1 hour equivalent to the time taken to introduce the reagent(s), i.e. the brominating agent or a mixture of brominating agent/compound of formula II, into the reaction medium.

On the other hand, at temperatures ranging from about 0° C. to about 15° C., the reaction is complete in about 1.5 hours if the reagent-introduction time is also about 1 hour.

Consequently, it is observed that the reaction according to the invention is virtually instantaneous at temperatures of about 35° C. to 45° C., in particular at the reflux temperature of dichloromethane. In addition, at temperatures from about 0° C. to about 15° C., the reaction time remains entirely compatible with industrial development.

For comparative purposes, the photo-bromination of OTBN was carried out with bromine at a temperature of 40° C. either in dichloromethane alone or in a two-phase medium according to the invention, i.e. consisting of water and dichloromethane, in order to form 4'-bromomethyl-2-cyanobiphenyl, referred to hereinbelow as Compound A.

In both cases, the same reaction conditions were observed and the introduction of bromine into the reaction medium containing OTBN takes about 1 hour.

The results below were obtained, expressed as % of OTBN, of Compound A and of 4'-dibromomethyl-2-cyanobiphenyl (referred to hereinbelow as "dibromo compound") found in the reaction medium:

a) in dichloromethane alone

| Time (min) | OTBN remaining (%) | Compound A formed (%) | Dibromo compound formed (%) |
| --- | --- | --- | --- |
| 15 | 99.7 | 0.3 | 0 |
| 30 | 73.4 | 26.1 | 0.5 |
| 60 | 46.5 | 53 | 0.5 |
| 120 | 13.6 | 80.6 | 5.8 |
| 180 | 9.5 | 82.9 | 7.6 | b) in the two-phase medium according to the invention

| Time (min) | OTBN remaining (%) | Compound A formed (%) | Dibromo compound formed (%) |
| --- | --- | --- | --- |
| 15 | 60.10 | 39.90 | 0 |
| 30 | 31.78 | 66.02 | 2.2 |
| 57 | 8.44 | 83.92 | 7.64 |
| 120 | 8.40 | 84.18 | 7.42 |

These results show:
that the reaction according to the invention is instantaneous at the temperature used since the final yield is virtually obtained at the end of introduction of the reagents
that the process of the prior art takes at least 3 hours in order to obtain a yield of Compound A close to the yield obtained after 1 hour by carrying out the process according to the invention.

Other comparative OTBN photo-bromination tests were carried out at 10° C. in a water/dichloromethane two-phase medium with a hydrobromic acid/sodium bromate system as brominating agent compared with a hydrobromic acid/hydrogen peroxide system.

The results showed that the reaction with the hydrobromic acid/hydrogen peroxide system give a conversion of OTBN into Compound A of only 20% after 1.5 hours. By contrast, under the same conditions, a degree of conversion of 85% of OTBN into Compound A is also recorded after 1.5 hours. In addition, the bromination starting with hydrobromic acid/sodium bromate was found to be virtually instantaneous.

Moreover, the results showed that at the end of the reaction, the selectivity towards Compound A is better with the hydrobromic acid/sodium bromate system than with the hydrobromic acid/hydrogen peroxide system.

Finally, the monobromo derivatives of formula I obtained according to the process of the invention thus described can be subsequently separated from the reaction medium according to conventional methods, for example by separating out the organic phase after settling of the phases, removal of the solvent and optionally recrystallization in a suitable medium or alternatively by chromatographic methods.

The process of the invention can be carried out in various ways by using, depending on the case, techniques of batchwise or continuous type.

For example, the preparation of the compounds of formula I according to the invention can be envisaged by implementation in a batchwise phase involving:
1) either the total loading, into the reactor, of the various constituents of the two-phase medium as well as the reagents, i.e. the substrate of formula II and the brominating agent, followed by irradiation of the reaction medium 2) or the loading of the various constituents of the two-phase medium, followed by the introduction, into this medium maintained under irradiation, of a mixture of the reagents, optionally dissolved or suspended in the organic solvent, 3) or, on the contrary, the introduction by adding the brominating agent optionally dissolved or suspended in the organic solvent, into the reaction medium maintained under irradiation, this medium consisting of the two-phase mixture containing the substrate of formula II. In the case of a brominating agent formed from hydrobromic acid/alkali metal bromate, it is also possible to envisage introduction by adding hydrobromic acid to a reaction medium under light irradiation, this medium consisting of the two-phase mixture of the alkali metal bromate and the substrate of formula II.

In order to carry out the process of the invention according to a batchwise method, use may be made of a device comprising a reactor of conventional type equipped with a heating or cooling jacket and designed so as preferably to allow immersion of the light source into the reaction medium.

In the context of development of the process of the invention, an increase in the selectivity toward monobromo derivative of formula I can be observed when the reaction temperature decreases, but also when the reagents are mixed together in total before introduction into the reactor.

However, the implementation of the process of the invention by introducing the mixture of reagents as envisaged in the batchwise techniques 2) and 3) described above requires virtually perfect control of the amount of photochemical initiator in order to control the reaction kinetics. Since the power of the lamps responsible for this photochemical initiation is not adjustable, it consequently turns out to be necessary to irradiate small volumes of this medium, the temperature of which is more easily controlled.

On account of these constraints, it may favourably be envisaged to carry out the process of the invention in continuous phase.

Thus, use may be made, for the bromination reaction, of continuous-phase implementations based on a circulation of reagents consisting of the brominating agent and the biphenyl derivative of formula II, in a tubular piston-flow reactor ("plug-flow reactor"), i.e. a reactor with flow such that each fluid element crosses the reactor without mixing with the previous one or the subsequent one, this reactor being photo-irradiated and maintained at a temperature of between 0° C. and 45° C., for example at a temperature of between 0° C. and room temperature, preferably at a temperature of between 0° C. and 15° C.

To this end, a suitable device which allows, for example, the introduction, at controlled flow rate and into a two-phase medium, of a solution or suspension of substrate of formula II and of brominating agent optionally in the organic solvent chosen, may advantageously be used, the flow rate being adjusted by means of an assembly composed of a metering pump and a flow regulator coupled to a balance. This device is also completed by a reactor comprising an inlet, for the introduction of the various constituents of the reaction medium, and an outlet for collecting the products derived from the reaction. This reactor, which is intended to receive the two-phase medium, consists of a tube made, for example, of glass or quartz, preferably in the form of a spiral, immersed in a heating or cooling fluid, for example a bath of water containing or not containing glycol, the temperature of which is controlled by means of a cryothermostat.

In such a device, when it is a helical reactor, the lamp required for photoirradiation of the reaction medium, for example a mercury vapour lamp, can be positioned outside or, preferably, inside the tubular volume formed by this reactor, but, however, in the immediate vicinity of this reactor.

Certain brominating agents used in the process of the invention can give rise to water-soluble by-products. Such is the case in particular for DBDMH, which gives 5,5-dimethylhydantoin (referred to hereinbelow as DMH) which is water-soluble but crystallizes, however, in the medium if the degree of conversion of the compound of formula II into the monobromo compound of formula I is greater than 80%.

This crystallization consequently entails clogging of the tubular reactor, which disrupts the plug-flow of the reaction medium.

Consequently, it may be advantageously envisaged to complete the process of the invention by an operation of continuous extraction of the water-soluble by-products derived from the bromination reaction, their removal from the reaction medium and, if necessary, their recovery.

Consequently, and according to a preferred implementation of the invention, the bromination reaction and the extraction of the water-soluble by-products derived from this reaction are carried out simultaneously and in continuous phases, the by-products then being removed from the reaction medium.

To this end, a tubular plug-flow reactor consisting of a liquid/liquid extraction column is advantageously used.

These operations can be carried out according to a technique involving, on the one hand, the continuous-phase bromination reaction by circulation of the reaction mixture formed by the organic solvent and the reagents, in a tubular plug-flow reactor consisting of a liquid/liquid extraction column which is photo-irradiated and maintained at a temperature of between 0° C. and 45° C., for example at a temperature of between 0° C. and room temperature, preferably at a temperature of between 0° C. and 15° C., and, on the other hand, the simultaneous and continuous extraction of the water-soluble by-products, this being carried out by the water of the two-phase medium circulating counter-currentwise relative to the said reaction mixture in the column, as well as the removal of the water-soluble by-products in question from the reaction medium.

This method makes it possible in particular to increase the selectivity of the bromination reaction and to improve its temperature control by removing, if necessary, the heat evolved by the lamp and by the reaction.

Another subject of the invention consequently relates to a photo-bromination device for carrying out the process of the invention in the continuous phase, comprising a tubular plug-flow reactor consisting of a liquid/liquid extraction column photoirradiated and maintained at a temperature of between 0° C. and 45° C., for example at a temperature of between 0° C. and room temperature, preferably at a temperature of between 0° C. and 15° C.

BRIEF DESCRIPTION OF DRAWING

Other characteristics and advantages will become apparent in the course of the description below of one embodiment of the device of the invention, given by way of non-limiting example, with regard to the attached drawing in which the FIG. 1 represents a schematic view of such a continuous photo-bromination device.

The device described is particularly suitable for carrying out a process using halogenated aromatic or aliphatic hydrocarbons as water-immiscible organic solvents.

Figure 1:
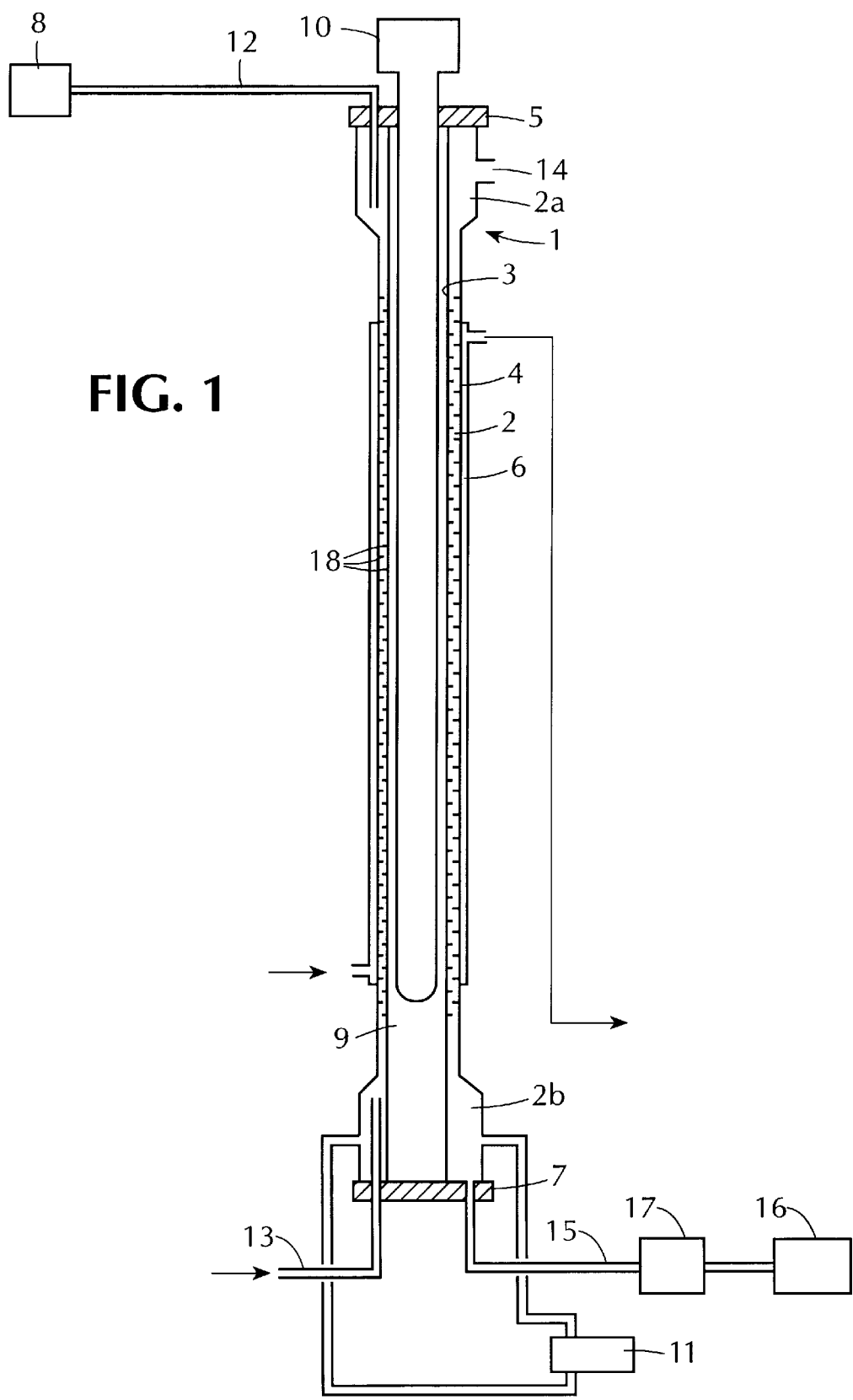

With reference to this figure, the device comprises a reactor (1) forming a liquid/liquid extraction column for example made of glass or quartz.

This reactor consists of a circular chamber (2) with a vertical axis, delimited by an inner wall (3) and an outer wall (4) which are spaced apart. At the top and bottom parts, respectively, of the reactor are a chamber (2) comprising two decanters (2a) and (2b) or standing zones for separating the two phases. Two discs (7) and (5) close the bottom and top ends respectively of the chamber (2). The outer wall (4) is, in its central part, in contact with a heat exchanger (6). According to one preferred embodiment of the invention, the circular chamber (2) is equipped in its outer central part with a jacket in which circulates a cooling or heating liquid, for example an aqueous glycol solution.

The inner wall (3) and the discs (7) and (5) delimit an inner chamber (9) in which is placed a photochemical lamp (10), for example a mercury-vapour lamp, equipped with a jacket (not represented) in which circulates a cooling liquid, for example deionized water. Alternatively, the photochemical lamp (10) lacks such a jacket. In this case, the cooling of this lamp can be ensured by a circulation of liquid provided for this purpose in the chamber (9).

The lamp (10) passes through the disc (5) to which it is attached.

The reactor also comprises a supply pipe (12) for loading the reagents and the organic solvent, which is located at the top of the column, as well as a water-supply pipe (13) at the bottom of the column. The water-supply pipe (13) passes through the disc (7) and emerges in the lower decanter (2b) of the chamber (2) below the level of the lamp (10). The supply pipe (12) passes through the disc (5) and emerges in the upper decanter (2a) of the chamber (2).

The reactor also comprises an outlet (14) for removing the aqueous solution to remove the water-soluble by-products. This outlet is located at the top of the column and consists, for example, of a discharge pipe passing through the outer wall (4) of the chamber (2) into the upper decanter (2a). A pipe (15) for removing the reaction products moreover passes through the disc (7). The opposite faces of the inner wall (3) and outer wall (4) of the chamber (2) preferably comprise protruding portions consisting, for example, of interleaved half-discs arranged along the central part of the chamber (2), forming chicanes (18).

These half-discs are made of an inert material, for example a suitable plastic such as polytetrafluoroethylene. Alternatively, the packing in the form of chicanes is comoosed of crowns or discs supported by rods (not represented) fixed to the discs (5) and (7), the space between these crowns or discs being adjustable by struts of defined height.

Furthermore, the photo-bromination device can be equipped, upstream of the supply pipe (12), with a tank (8) intended for storing the reagents and the organic solvent and, downstream of the discharge pipe (15), with a second tank (16) for storing, after removal, the brominated products formed during the reaction.

Advantageously, this device comprises a hydraulic guard (17) located immediately at the column exit, downstream of the discharge pipe (15) and mounted in series with the tank (16). This hydraulic guard is intended to maintain the organic phase continuously in the chamber (2) in order to carry out the photo-bromination with plug-flow, water constituting the dispersed phase.

This dispersion, obtained by means of the chicanes, is, however, improved by pulsation of the reaction mixture, brought about by means of a metering pump (11), for example a membrane pump, connected to the lower decanter (2b) of the chamber (2).

During a use of this device, the chamber (2) is prefilled with the organic solvent. The lamp (10) is lit and its cooling circuit is switched on.

When it is present, the metering pump (11) is switched on so as to ensure pulsation of the reaction mixture in the chamber (2).

The chamber (2) is then brought to a desired temperature by means of the corresponding heating or cooling system.

The column is then fed continuously with water, on the one hand, and with organic solution of the reagents, on the other hand.

The use of the device for simultaneous bromination and extraction thus designed, to carry out the process of the invention in continuous phase, makes it possible to obtain monobromo derivatives of formula I in excellent selectivity and with a particularly high degree of conversion of the compound of formula II into the desired compound.

For example, the degree of conversion of the OTBN into 4'-bromomethyl-2-cyanobiphenyl is greater than or equal to 90% and the selectivity towards the desired compound is between 85 and 90%, whereas the level of corresponding dibromo compound is less than 10%, generally about 5 to 7%.

Among the by-products derived from the reaction, those originating from the decomposition of the brominating agent can be advantageously recovered, reconverted and recycled, for example into the process of the invention.

This is the case in particular for DMH, a water-soluble product derived from the decomposition of DBDMH. This product, after reconversion into DBDMH, for example by treatment using bromine in basic medium, can be recycled in particular in a continuous implementation of the process of the invention.

For example, at 10° C., such a treatment in the presence of sodium hydroxide or sodium carbonate gives 91 to 92% of DBDMH with a purity of greater than 99%.

This possibility of recovering and recycling reaction by-products after retreatment adds to the advantage represented by carrying out the process of the invention in continuous phase described previously when it makes use of a liquid/liquid extraction column as plug-flow bromination reactor.

The non-limiting examples below illustrate the invention.

In these examples, the in-process reaction controls were performed by high performance liquid chromatography, referred to hereinbelow as HPLC, on the reaction medium diluted in acetonitrile.

In addition, the expression "dibromo compound" also denotes herein 4'-dibromomethyl-2-cyanobiphenyl which is also produced during the bromination reaction.

EXAMPLE 1

4'-Bromomethyl-2-cyanobiphenyl 200 g (1.036 mol) of OTBN, 1000 ml of dichloromethane and 600 ml of water are introduced into a 2 liter glass reactor equipped with a jacket connected to a cryothermostat for controlling the internal temperature, a stirrer of turbomixer type and a medium-pressure mercury vapour lamp (power: 150 watts) located in a dip tube cooled by means of a circulation of water in a jacket, and the assembly is then placed under stirring.

The lamp is switched on, the reaction medium is heated by it to boiling point and, while adjusting the feed rate, a suspension of 162.2 g (0.567 mol) of DBDMH in 200 ml of dichloromethane is then introduced over 1 hour.

The medium is maintained at reflux during the introduction and then for a further 1 hour. The reaction mixture is cooled to between 20 and 25° C., the stirring is stopped and the phases are allowed to separate by settling for 30 min.

The upper aqueous phase is removed and the organic phase is washed twice with 2000 ml of water.

An HPLC control gives the following results:

| OTBN | desired compound | dibromo compound |
|------|------------------|------------------|
| 3.5% | 86%              | 10.5%            |

The desired compound is then isolated after partial removal of the dichloromethane, addition of 250 ml of methyl tert-butyl ether, removal of the dichloromethane while keeping the volume constant by successive addition of 250 ml fractions of methyl tert-butyl ether (final % of dichloromethane<2.5), cooling to 20° C., filtration, spin-drying, washing with 150 ml and then 70 ml of methyl tert-butyl ether and oven-drying at 50° C. under vacuum.

In this manner, 224.5 g of 4'-bromomethyl-2-cyanobiphenyl are obtained in the form of a beige powder.

Yield: 79.6%

EXAMPLE 2

4'-Bromomethyl-2-cyanobiphenyl 150 g (0.776 mol) of OTBN, 700 ml of dichloromethane and 300 ml of water are introduced into a glass reactor equipped as described in Example 1, and the assembly is then placed under stirring at 300 rpm. The mercury vapour lamp is switched on and, while adjusting the feed rate, a solution of 124 g (0.776 mol) of bromine in 200 ml of dichloromethane is then introduced over 1 hour. The medium is maintained at reflux throughout the introduction.

An HPLC control carried out after 57 min shows that the medium contains:

| OTBN  | desired compound | dibromo compound |
|-------|------------------|------------------|
| 8.44% | 83.92%           | 7.64%            |

The medium is maintained at reflux for a further 1 hour and is then cooled to between 20 and 25° C. The stirring is stopped and the phases are allowed to separate by settling for 30 min.

The upper aqueous phase is removed and the organic phase is washed twice with water.

A further HPLC control gives the following results after 2 hours of reaction:

| OTBN | desired compound | dibromo compound |
|------|------------------|------------------|
| 8.4% | 84.18%           | 7.42%            |

EXAMPLE 3

4'-Bromomethyl-2-cyanobiphenyl 200 g (1.036 mol) of OTBN, 900 ml of dichloromethane and 400 ml of water are introduced into a glass reactor equipped as in Example 1, and the assembly is then placed under stirring at 380 rpm.

The medium is cooled to a temperature of between 0° C. and 5° C. and the mercury vapour lamp is then switched on while maintaining the reaction medium at the same temperature. While controlling the feed rate, a solution of 165.4 g (1.03 mol) of bromine in 300 ml of dichloromethane is then introduced over about 1 hour.

The medium is maintained at a temperature of between 0° C. and 5° C. throughout the introduction.

At the end of introduction, i.e. after 58 min, an HPLC control of the coloured reaction medium shows that it contains:

| OTBN   | desired compound | dibromo compound |
|--------|------------------|------------------|
| 34.05% | 64.66%           | 1.29%            |

The stirring is continued, which gives, 30 minutes after the end of introduction, an orange-coloured medium containing:

| OTBN   | desired compound | dibromo compound |
|--------|------------------|------------------|
| 14.16% | 82.60%           | 3.24%            |

60 min after the end of introduction, this same medium, which has turned yellow, contains:

| OTBN  | desired compound | dibromo compound |
|-------|------------------|------------------|
| 6.53% | 88.42%           | 5.05%            |

EXAMPLE 4

4'-Bromomethyl-2-cyanobiphenyl 250 g (1.29 mol) of OTBN, 1000 ml of dichloromethane and 500 ml of water are introduced into a 2 liter glass reactor equipped as described in Example 1, and the assembly is then placed under stirring at 300 rpm. The medium is cooled to 10° C. by circulation of glycol-water in the jacket and 64.9 g (0.43 mol) of sodium bromate are then added.

The mercury vapour lamp is switched on and the introduction of 222 g of 47% hydrobromic acid (corresponding to 104.4 g of 100% acid, i.e. 1.29 mol) is then started, by means of a metering pump and a flow regulator (flow rate: 222 g/h).

At the end of introduction of the hydrobromic acid, i.e. after 60 min, the orange-coloured medium contains:

| OTBN   | desired compound | dibromo compound |
|--------|------------------|------------------|
| 32.27% | 66.27%           | 1.46%            |

This medium is maintained at 10° C. with stirring for a further 60 min, and a mixture is thus obtained containing:

| OTBN | desired compound | dibromo compound |
|---|---|---|
| 5.62% | 88.02% | 6.36% |

EXAMPLE 5

4'-Bromomethyl-2-cyanobiphenyl a) Preparation 100 kg of OTBN and 81.2 kg (1.1 equivalents) of DBDMH are loaded into a tank, followed by addition of 2000 l of dichloromethane.

The assembly is placed under stirring at 60 to 80 rpm and is maintained at 20° C. to 25° C. until dissolution is complete.

b) Photo-bromination

A device comprising a circular tubular plug-flow reactor in the form of a liquid/liquid extraction column as illustrated in the attached figure is used for this operation.

This column is filled with dichloromethane, the power of the lamp is adjusted to 6 kw, the column is pressurized to 0.3 bar and its specific cooling circuit using deionized water is then switched on.

The lamp is switched on and the pulsation system for the reaction mixture in the column is switched on, adjusting the pulsation frequency to 30% (=15 Hz) and the course frequency to 20%.

Circulation of glycol-water in the pulsed-column jacket is switched on and the flow rates of glycol-water are adjusted until a temperature of 10° C. in the dichloromethane medium is obtained.

Continuous feeding of the pulsed column is then started, first with deionized water at a rate of 300 kg/h and then with a solution of OTBN/DBDMH in the dichloromethane prepared in paragraph a) above, at a rate of 600 kg/h.

These operating conditions are maintained until the solution of the reagents in the chloromethane has been depleted, followed by rinsing the tank which contained this solution and the transfer line up to the column and the column itself th 200 l of dichloromethane.

An HPLC analysis shows that the mixture at the end of reaction contains:

| OTBN | desired compound | dibromo compound |
|---|---|---|
| 5.7% | 87.5% | 6.8% | a) Isolation

The desired compound is then isolated by washing the solution of the photo-brominated products in dichloromethane with a dilute aqueous sodium bisulphite solution, recovery of the organic phase by separation of the phases after settling, preconcentration of this organic phase, removal of the dichloromethane by successive additions of methyl tert-butyl ether, crystallization of the suspension at 0° C. to 3° C., filtration, spin-drying of the suspension, washing of the product obtained with methyl tert-butyl ether and drying at 40 to 45° C.

In this manner, pure 4'-bromomethyl-2-cyano-biphenyl is obtained in a yield of 78% by weight relative to the OTBN.

What is claimed is:

1. A process for preparing 4'-bromomethyl-biphenyl derivatives of general formula:

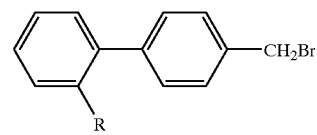

I in which R represents:
  a cyano group
  a group:

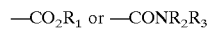

—CO$_2$R$_1$ or —CONR$_2$R$_3$ in which R$_1$, R$_2$ and R$_3$, which may be identical or different, represent hydrogen or a linear or branched C$_1$–C$_6$ alkyl group which can be optionally substituted with a halogen atom, a hydroxyl, amino, C$_1$–C$_4$ alkoxy group or with 1 to 3 phenyl groups optionally substituted with 1 to 3 groups chosen from halogen atoms and hydroxyl, nitro, C$_1$–C$_4$ alkyl and C$_1$–C$_4$ alkoxy groups,
  a tetrazolyl group of general formula:

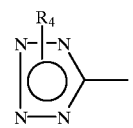

in which R$_4$, in position 1 or 2 of the tetrazolyl group, represents hydrogen or a protecting group, wherein a brominating agent chosen from bromine, N-bromoacetamide, N-bromophthalimide, N-bromomaleimide, an N-bromosulphonamide, N-bromosuccinimide, 1,3-dibromo-5,5-dimethylhydantoin and a hydrobromic acid/alkali metal bromate system is reacted, in a two-phase medium and under the effect of a photo-irradiation, with a biphenyl derivative of general formula:

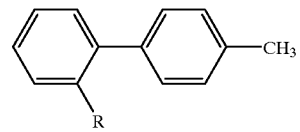

II in which R has the same meaning as above, which gives the desired compound.

2. A process according to claim 1 wherein R represents a tetrazolyl group in which R$_4$ represents a linear or branched C$_1$–C$_6$ alkyl group optionally substituted with 1 to 3 phenyl groups which are themselves optionally substituted with 1 to 3 groups chosen from halogen atoms and hydroxyl, nitro, C$_1$–C$_4$ alkyl and C$_1$–C$_4$ alkoxy groups.

3. A process according to claim 1 wherein R represents a cyano, tetrazolyl or triphenylmethyltetrazolyl group or a group —CO$_2$R$_1$ in which R$_1$ represents hydrogen or a methyl, ethyl or propyl group.

4. A process according to claim 3 wherein R represents a cyano group.

5. A process according to claim 1 wherein the two-phase medium consists of water and of one or more water-immiscible organic solvents.

6. A process according to claim 5 wherein the organic solvent is a halogenated aliphatic hydrocarbon or a halogenated aromatic hydrocarbon.

7. A process according to claim 6 wherein the organic solvent is diechloromethane.

8. A process according to claim 1 wherein the two-phase medium comprises from 0.1 to 1 volume of water per volume of organic solvent.

9. A process according to claim 8 wherein the two-phase medium is used in a proportion of from 3 to 30 equivalents by volume per equivalent by weight of biphenyl derivative of formula II.

10. A process according to claim 1 wherein the brominating agent is bromine, N-bromosuccinimide, 1,3-dibromo-5,5-dimethyl-hydantoin or a hydrobromic acid/alkali metal bromate system.

11. A process according to claim 1 wherein the brominating agent is used at a rate of from 0.5 to 1.4 molar equivalents per molar equivalent of biphenyl derivative of formula II.

12. A process according to claim 11 wherein the brominating agent is used at a rate of from 0.95 to 1.1 molar equivalents per molar equivalent of biphenyl derivative of formula II.

13. A process according to claim 12 wherein the alkali metal bromate is used at a rate of from 0.3 to 0.4 molar equivalent per molar equivalent of biphenyl derivative of formula II.

14. A process according to claim 1 wherein the reaction is carried out at a temperature of between 0° C. and 45° C.

15. A process according to claim 14 wherein the reaction is carried out at a temperature of between 0° C. and room temperature.

16. A process according to claim 15 wherein the reaction is carried out at a temperature of between 0° C. and 15° C.

17. A process according to claim 1 wherein the photo-irradiation is obtained using a light source which emits radiation of 360 to 600 nm.

18. A process according to claim 1 wherein the bromination reaction takes place in continuous phase and comprises the continuous circulation of the reagents consisting of the brominating agent and the biphenyl derivative of formula II in a tubular plug-flow reactor, this reactor being photo-irradiated and maintained at a temperature of between 0° C. and 45° C., which gives the desired compound and possibly water-soluble by-products.

19. A process according to claim 18 wherein the bromination reaction and the extraction of the water-soluble by-products, which are then removed from the reaction medium, are carried out simultaneously and in continuous phases.

20. A process according to claim 19 wherein the reaction, the extraction and the removal are carried out in a plug-flow reactor consisting of a liquid/liquid extraction column.

21. A process according to claim 18 wherein it comprises, on the one hand, the continuous-phase bromination reaction by circulation of the mixture formed by the organic solvent and the reagents, in a tubular plug-flow reactor consisting of a liquid/liquid extraction column which is photo-irradiated and maintained at a temperature of between 0° C. and 45° C., and, on the other hand, the simultaneous and continuous extraction of the water-soluble by-products, this being carried out using the water from the two-phase medium circulating counter-currentwise relative to the said mixture in the column, followed by the removal of the said water-soluble by-products from the reaction medium.

22. A process according to claim 18 wherein the temperature is between 0° C. and room temperature.

23. A process according to claim 18 wherein the temperature is between 0° C. and 15° C.

\* \* \* \* \*